US00PP09525P

United States Patent [19]

Austin

[11] Patent Number: Plant 9,525

[45] Date of Patent: Apr. 30, 1996

[54] SHRUB ROSE PLANT NAMED 'AUSSAL'

[75] Inventor: David C. H. Austin, Albrighton, England

[73] Assignee: Davis Austin Roses Limited, England

[21] Appl. No.: 404,161

[22] Filed: Mar. 14, 1995

[51] Int. Cl.[6] ..... A01H 5/00

[52] U.S. Cl. ..... Plt./1

[58] Field of Search ..... Plt./1, 22, 26

[56] References Cited

U.S. PATENT DOCUMENTS

P.P. 8,671 4/1994 Austin ..... Plt./1

P.P. 9,261 8/1995 Olesen et al. ..... Plt./1

*Primary Examiner*—Howard J. Locker

*Attorney, Agent, or Firm*—Klarquist Sparkman Campbell Leigh & Whinston

[57] ABSTRACT

A shrub rose having medium, old-fashioned-shaped flowers that are repeat flowering, generally rich, clear pink in color, the color of the petals varying on each flower.

1 Drawing Sheet

The present invention relates to a new and distinct variety of rose plant of the shrub class which was originated by me by crossing an unnamed variety with another unnamed variety.

The primary objective of this breeding was to produce a new repeat flowering shrub rose with old-fashioned-shaped flowers. The objective was substantially achieved, along with other desirable improvements, as evidenced by the following unique combination of characteristics that are outstanding in the new variety and that distinguish it from its parents, as well as from all other varieties of which I am aware:

1. Very full, old-fashioned-shaped flowers.
2. Rich, clear pink flowers.
3. Bushy growth.

Asexual reproduction of this new variety by budding, as performed at Albrighton, Wolverhampton, England, shows that the foregoing and all other characteristics and distinctions come true to form and are established and transmitted through succeeding propagations.

The accompanying illustration shows typical specimens of the vegatative growth and flowers of this new variety in different stages of development, depicted in color as nearly true as it is reasonably possible to make the same in a color illustration of this character.

The following is a detailed description of my new rose cultivar with color descriptions using terminology in accordance with The Royal Horticultural Society (London) Colour Chart, except where ordinary dictionary significance of color is indicated.

Parentage:

*Seed parent.*—Unnamed variety.

*Pollen parent.*—Unnamed variety.

Classification:

*Botanical.*—*Rosa hybrida.*

*Commercial.*—Shrub.

FLOWER

Observations made from specimens grown in a garden environment at Albrighton, Wolverhampton, England.

Blooming habit: Recurrent.

Bud:

*Size.*—About 2.5 to 3.0 cm long when the petals start to unfurl.

*Form.*—The bud form is pointed ovoid and globular.

*Color.*—When sepals first divide, bud color is Red Group 39B. When half blown, the upper sides of the petals are Red Group 55C; and the lower sides of the petals are Red Group 51D.

*Sepals.*—Color: Yellow-green Group 144A. Surface texture: Slightly leathery. There are three (3) very lightly appendaged sepals. There are two unappendaged sepals with smooth downy edges.

*Receptacle.*—Color: Yellow-green Group 144A/B. Shape: Funnel or goblet. Size: Medium, about 8 to 10 mm long×7–8 mm wide. Surface: Smooth.

*Peduncle.*—Length: Medium, averaging about 4.5 cm. Surface: Glandular. Color: Light green or bronzy. Strength: Weak, bending.

Bloom:

*Size.*—Medium. Average open size is 6.5–7.5 cm.

*Borne.*—Several together in clusters of irregular shape.

*Stems.*—Medium. Average length is about 75 to 65 cm.

*Form.*—When first open: Slightly cupped. Permanence: Flattens; outer petals curl back; outer petal edges curl slightly.

*Petalage.*—Number of petals under normal conditions: 95 to 100.

*Color.*—The upper side of the petals is Red Group 55C. The reverse sidee of the petals is Red Group 55C. Basal ¼ to ⅓ of petals are yellowish, the yellow coloring deepening toward basal tip. The major color on the upper side is Red Group 55C.

*Variegations.*—None.

*Discoloration.*—The general tonality at the end of the first day: Paler, less salmon, more pink. At the end of the third day: Red 56 GroupA/B.

*Fragrance.*—Strong.

Petals:

*Texture.*—Firm and thin.

*Shape.*—Notched, deltoid.

*Form.*—Fairly flat, tips slightly recurved.

*Arrangement.*—Informal or quartered, with few petaloids in the center. Inner petals tend to be tucked into calyx to form button.

*Persistence.*—Petals drop off cleanly before drying.

*Lastingness.*—On the plant: Fair, about 3 days. As a cut flower: Fair, 2 to 3 days.

Reproductive parts:

*Anthers.*—Size: Medium. Quantity: Many. Color: Yellow. Arrangement: Tucked in calyx or partly so.
*Filaments.*—Color: Reddish (cerise).
*Pollen.*—Color: Gold yellow.
*Styles.*—Color: Base: greenish white; Top: Cerise.
*Stigmas.*—Color: Yellow.

Form: Shrub.

Growth: Medium to vigorous, branching and sprawling. Mature plant about 75 cm in height and 90 cm in width.

Foliage:
*Number of leaflets on normal mid-stem leaves.*—5.
*Size.*—Medium to large (about 17–18 cm long×14 cm wide).
*Quantity.*—Normal.
*Color.*—New foliage: Green Group 146A/B with bronzy/reddish blush. Old foliage: Green Group 147A.

Leaflets:
*Shape.*—Pointed oval.
*Texture.*—Upper side: Leathery.
*Edge.*—Serrated.
*Serration.*—Double.
*Petiole rachis.*—Color: Green.
*Petiole underside.*—With prickles, 2 to 4 per internode.
*Stipules.*—Medium (2.5 to 3.0 cm long), serrated.
*Disease resistance.*—Resistant to mildew and blackspot under normal growing conditions at Albrighton, Wolverhampton, England.

Wood:
*New wood.*—Color: Dark green, reddish. Bark: Smooth
*Old wood.*—Color: Green. Bark: Smooth.

Prickles:
*Quantity.*—On main canes from base: Many On laterals from main canes: Few.
*Form.*—Medium length; straight or slightly hooked downward.
*Color when young.*—Red.
*Position.*—Evenly distributed around stem.

Small Prickles:
*Quantity.*—On main stalks: Few. On laterals: Few.
*Color.*—Brown.

I claim:

1. A new and distinct variety of rose plant of the shrub class, substantially as herein shown and described, characterized particularly as to novelty by the unique combination of its repeat flowering, with old-fashioned-shaped flowers that are generally rich, clear pink flowers, the color of the petals varying on each flower.

* * * * *

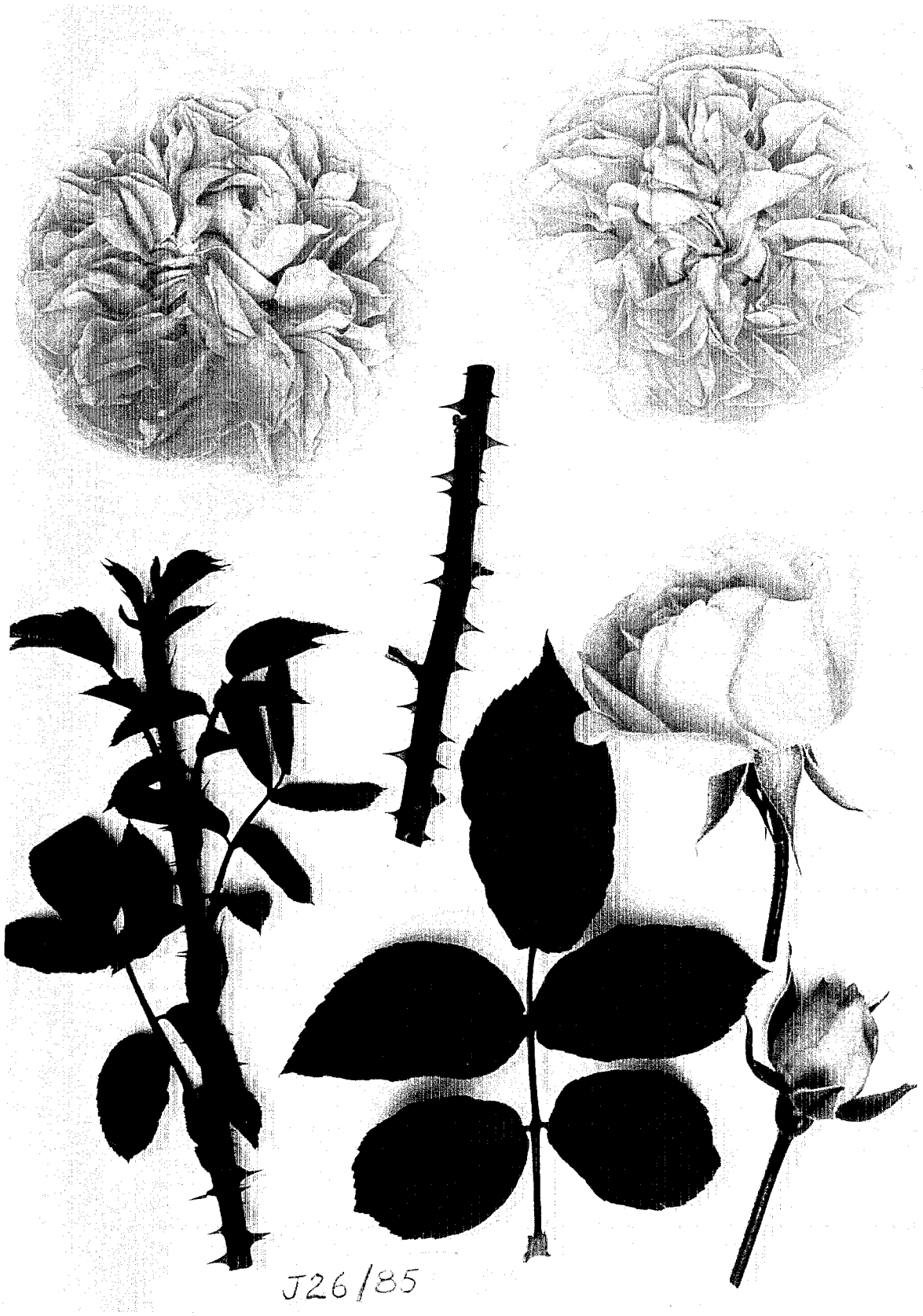
J26/85

UNITED STATES PATENT AND TRADEMARK OFFICE

CERTIFICATE OF CORRECTION

PATENT NO. : Plant 9,525

DATED : April 30 , 1996

INVENTOR(S) : David C.H. Austin

It is certified that error appears in the above-indentified patent and that said Letters Patent is hereby corrected as shown below:

Column 2, line 25, "sidee" should read --side--.

Column 4, line 8, "Many On laterals" should read --Many to ordinary. On--.

Column 4, line 9, "Few." should read --Ordinary to few.--.

Signed and Sealed this

Sixteenth Day of September, 1997

*Attest:*

Bruce Lehman

BRUCE LEHMAN

*Attesting Officer*

*Commissioner of Patents and Trademarks*